United States Patent [19]

Dobrovolny et al.

[11] Patent Number: 5,704,900

[45] Date of Patent: Jan. 6, 1998

[54] METHOD AND APPARATUS FOR PERITONEAL DISTENSION

[75] Inventors: Walter J. Dobrovolny; Steven M. LeVahn, both of St. Paul, Minn.

[73] Assignee: Minnesota Scientific, Inc., Minneapolis, Minn.

[21] Appl. No.: 546,081

[22] Filed: Oct. 20, 1995

[51] Int. Cl.$^6$ ............................................. A61B 11/02
[52] U.S. Cl. ........................ 600/229; 600/227; 600/228; 600/235
[58] Field of Search ................................ 600/204, 209, 600/210, 208, 206, 201, 226, 227, 228, 229, 230, 235; 248/422; 254/95, 97; 269/61, 74, 76; 5/600, 621, 630

[56] References Cited

U.S. PATENT DOCUMENTS

| | | | |
|---|---|---|---|
| 1,400,616 | 12/1921 | McCroby et al. | |
| 1,460,697 | 7/1923 | Bendlin | |
| 1,707,689 | 4/1929 | Sloan | |
| 1,747,799 | 2/1930 | Straus | |
| 1,902,401 | 3/1933 | Gunning | |
| 2,465,206 | 3/1949 | Davis | 304/9 |
| 2,594,086 | 4/1952 | Smith | 128/20 |
| 2,670,732 | 3/1954 | Nelson | 128/20 |
| 2,986,395 | 5/1961 | Sheftel | 273/1.5 |
| 3,196,865 | 7/1965 | Rose | 128/20 |
| 3,208,711 | 9/1965 | Pagliuso | 248/422 |
| 3,643,655 | 2/1972 | Peronti | 128/20 |
| 3,810,462 | 5/1974 | Szpur | 128/20 |
| 3,823,709 | 7/1974 | McGuire | 128/20 |
| 3,910,538 | 10/1975 | Baitella | 248/122 |
| 4,099,521 | 7/1978 | Nestor et al. | 128/20 |
| 4,143,652 | 3/1979 | Meier et al. | 128/20 |
| 4,254,763 | 3/1981 | McCreedy et al. | 128/20 |
| 4,254,928 | 3/1981 | Huempfner et al. | 248/422 |
| 4,355,631 | 10/1982 | LeVahn | 128/20 |
| 4,617,916 | 10/1986 | LeVahn et al. | 128/20 |
| 4,718,151 | 1/1988 | LeVahn et al. | 24/535 |
| 4,863,133 | 9/1989 | Bonnell | 248/278 |
| 4,926,849 | 5/1990 | Downey | 128/75 |
| 4,949,707 | 8/1990 | LeVahn et al. | 128/20 |
| 4,971,037 | 11/1990 | Pelta | 128/20 |
| 5,020,195 | 6/1991 | LeVahn | 24/514 |
| 5,080,088 | 1/1992 | LeVahn | 128/20 |
| 5,183,033 | 2/1993 | Wilk | 128/20 |
| 5,184,601 | 2/1993 | Putman | 128/4 |
| 5,242,240 | 9/1993 | Gorham | 403/391 |
| 5,318,012 | 6/1994 | Wilk | 128/20 |
| 5,353,785 | 10/1994 | Wilk | 128/20 |
| 5,372,147 | 12/1994 | Lathrop, Jr. et al. | 128/898 |
| 5,375,481 | 12/1994 | Cabrera et al. | 74/577 M |
| 5,400,772 | 3/1995 | LeVahn et al. | 128/20 |
| 5,415,159 | 5/1995 | Ortiz et al. | 128/20 |

*Primary Examiner*—Beverly M. Flanagan
*Attorney, Agent, or Firm*—Kinney & Lange, P.A.

[57] ABSTRACT

The present invention is a method and apparatus for performing peritoneal distension. The method includes providing a support structure on a surgical table, wherein the support structure includes a substantially vertical post and an arm assembly. A distal end of the arm assembly is positioned over a patient on the surgical table while the vertical post remains stationary. A peritoneal distension instrument extending from the arm assembly is coupled to a peritoneal structure of the patient. The peritoneum of the patient is distended by vertically raising the arm assembly while the post remains stationary relative to the surgical table. The apparatus is a surgical instrument support structure including a substantially vertical post having a gear rack disposed generally along the post's axis and an arm assembly movably coupled along the gear rack extending from the gear rack for holding a surgical instrument. The arm assembly includes a circular gear rotatably coupled to the arm assembly in engagement with the gear rack and a mechanism for rotating the circular gear, whereby rotation of the circular gear raises and lowers the arm assembly relative to the vertical post.

10 Claims, 8 Drawing Sheets

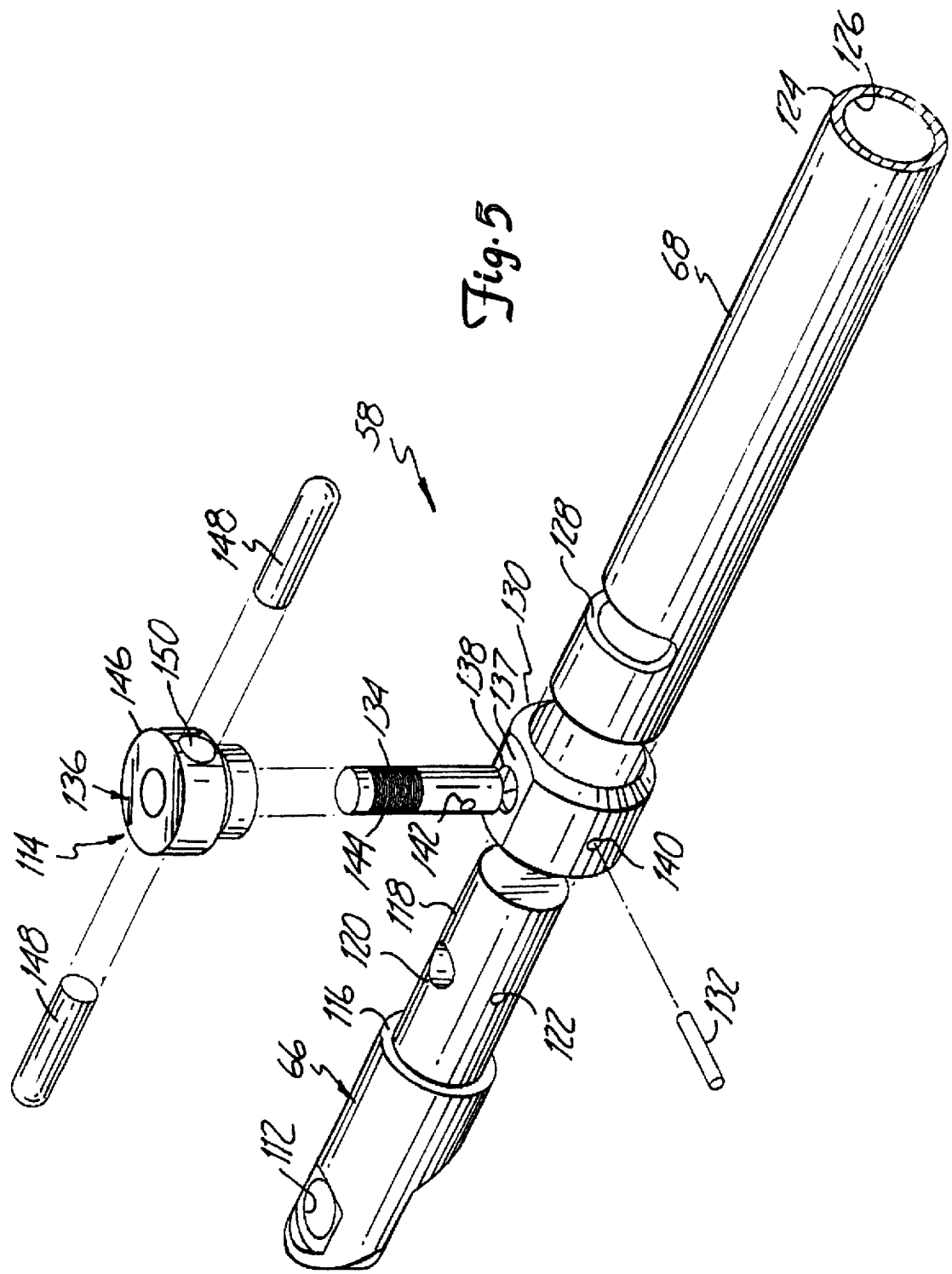

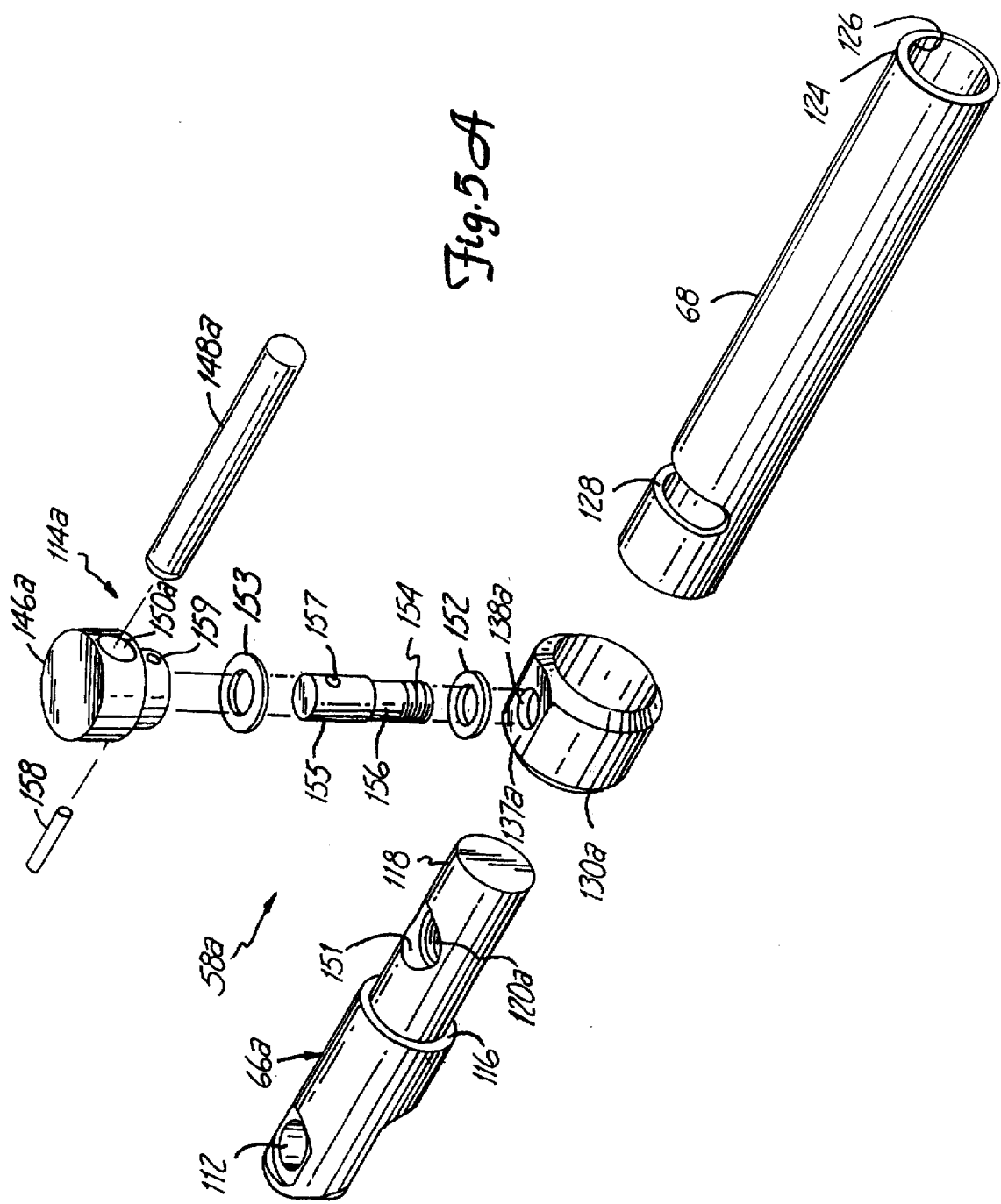

METHOD AND APPARATUS FOR PERITONEAL DISTENSION

BACKGROUND OF THE INVENTION

The present invention relates to surgical instrument support structures and their use. In particular, the present invention relates to a method and apparatus for performing peritoneal distension.

Laparoscopic surgery relates generally to surgical procedures performed through the abdominal wall. Laparoscopic surgery utilizes specialized instruments in conjunction with a laparoscope which are inserted through small incisions in the abdomen. During surgery, the physician observes manipulation of the instruments with the laparoscope. Because laparoscopic surgery is performed through small incisions, laparoscopic surgery is less traumatic, requires shorter surgical procedures and shorter recovery times than open surgical procedures.

During laparoscopic surgery, the abdominal wall typically must be lifted away from the underlying abdominal organs to improve the visibility and accessibility of the organs. Conventionally, the abdominal or peritoneal cavity is lifted or distended by insufflation whereby a physician injects gas through a needle into the peritoneum to inflate or tent-up the abdominal wall. To be effective, insufflation requires gas seals at all entry ports through the abdominal wall. Maintaining the required distension of the peritoneum is complicated by losses of gas through entry ports in the abdominal wall.

As an alternative to insufflation, mechanical lifts have been utilized to distend the peritoneum. Typically, the lift is introduced percutaneously into the peritoneum and elevated mechanically to distend the abdomen. Although effective, mechanical lifts are typically space consuming, unstable and difficult to set up and operate.

SUMMARY OF THE INVENTION

The present invention is a method and apparatus for performing peritoneal distension. The method includes providing a support structure on a surgical table, wherein the support structure includes a substantially vertical post and an arm assembly. A distal end of the arm assembly is positioned over a patient on the surgical table while the vertical post remains stationary. Peritoneal distension instruments extending from the arm assembly are coupled to a peritoneal structure of the patient. The peritoneum of the patient is distended by vertically raising the arm assembly while the post remains stationary relative to the surgical table.

The apparatus is a surgical instrument support structure including a substantially vertical post having a gear rack along its axis and an arm assembly movably coupled along the gear rack and extending from the gear rack for holding a surgical instrument. The arm assembly includes a circular gear rotatably coupled to the arm assembly in engagement with the gear rack and a mechanism for rotating the circular gear, whereby rotation of the circular gear raises and lowers the arm assembly relative to the vertical post.

In a preferred embodiment of the present invention, the support structure includes a pair of bearings frictionally engaging opposite sides of the substantially vertical post. The support structure of the preferred embodiment also includes a plurality of pin receiving detents circularly spaced about an axis of the circular gear and a locating pin in circular alignment with the plurality of pin receiving detents, whereby rotation of the circular gears causes relative rotation between the locating pin and the plurality of pin receiving detents and wherein insertion of the pin into one of the plurality of pin receiving detents prevents rotation of the circular gear.

As exemplified in the preferred embodiment of the present invention, a crank rotates the circular gear and pivotally supports the locating pin, whereby selective actuation of the crank pivots the pin in and out of engagement with a plurality of pin receiving detents. The arm assembly also includes a mechanism permitting adjacent portions of the arm assembly to be rotated relative to each other about an axis of the arm assembly.

BRIEF DESCRIPTION OF THE DRAWINGS

FIG. 5 is an exploded perspective view of a portion of the arm illustrated in FIG. 4.

FIG. 5A is an exploded perspective view of an alternate embodiment of the portion of the arm illustrated in FIG. 4.

DETAILED DESCRIPTION OF THE PREFERRED EMBODIMENTS

Throughout the specification of the application, various terms are used such as "upward", "downward", "vertical" and "horizontal". These terms denote directions with respect to the drawings and are not limitations of orientation of the present invention. These terms are provided for clarity in describing the relationship between members of the surgical instrument support structure.

Figure 1:
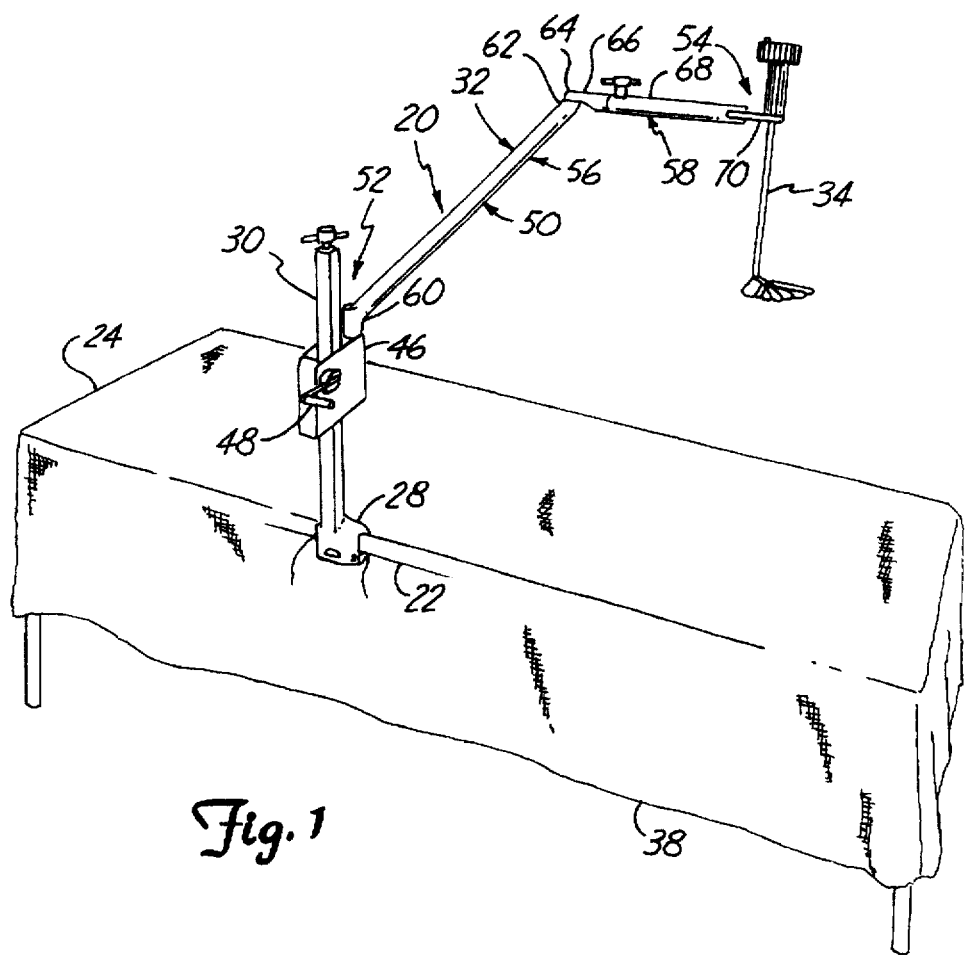
FIG. 1 is a perspective view illustrating a surgical instrument support structure of the present invention secured to a surgical table and supporting a distension instrument.

FIG. 1 illustrates a surgical instrument support structure 20 exemplifying the present invention secured to side rail 22 of an operating or surgical table 24. Support structure 20 supports an abdominal distension instrument 34 and generally includes clamping mechanism 28, post 30 and arm assembly 32. Clamping mechanism 28 rigidly secures post 30 to side rail 22. In addition to securing post 30 to table 24, clamping mechanism 28 also preferably secures a surgical drape 38 against side rail 22. Surgical drape 38 is a conventional surgical drape which has been sterilized. Surgical drape 38 is placed over a patient to prevent infection in the area of incision.

Post 30 is a generally elongate, rigid post coupled to clamping mechanism 28 and extending substantially vertically upward from clamping mechanism 28 above surgical table 24. Post 30 supports arm assembly 32 and distension instrument 34 above surgical table 24 while remaining substantially stationary or fixed relative to table 22, arm assembly 32 and distension instrument 34. Preferably, post 30 additionally provides a substantially vertical track or guiding member for regulating vertical movement of arm assembly 32 so that the physician may incrementally adjust the vertical height of arm assembly 32 relative to table 24 and post 30. As a result, vertical adjustment of arm 32 during surgery is stable, controlled and precise.

Arm assembly 32 extends generally horizontally from post 30 above table 24 to support distension instrument 34 above table 24 and above a patient (not shown). Arm assembly 32 is movably coupled to post 30 along post 30 for vertical adjustment and generally includes retractor support 46, adjustment mechanism 48 and retractor arm 50. Retractor support 46 is coupled between post 30 and retractor arm 50. Retractor support 46 serves as a carriage for carrying and guiding vertical movement of retractor arm 50 and any coupled surgical instruments such as distension instrument 34 along post 30. In addition, retractor support 46 engages post 30 and supports adjustment mechanism 48 to provide for precise incremental vertical adjustment of retractor arm 50 relative to post 30 and table 24. Once the vertical height of retractor arm 50 and distension instrument 34 has been set by adjustment mechanism 48, retractor support 46 locks and secures retractor support 46 to post 30 at a preselected height along post 30.

Adjustment mechanism 48 is coupled between retractor support 46 and post 30 for vertically raising and lowering retractor support 46 and retractor arm 50 relative to post 30 above table 24. Preferably, adjustment mechanism 48 is coupled to retractor support 46 in engagement with post 30 so that adjustment mechanism 48 is carried upward and downward with corresponding upward and downward movement of retractor support 46 and retractor arm 50. Once the vertical height of retractor support 46 and retractor arm 50 has been set, adjustment mechanism 48 rigidly engages post 30 to releasably lock or fix retractor support 46 and retractor arm 50 at the preselected height until further adjustment is necessary.

Retractor arm 50 is generally an elongate multi-segmented member having a proximal end 52 coupled to retractor support 46 and a distal end 54 supported above the patient on surgical table 24. Retractor arm 50 branches over table 24 from retractor support 46 and post 30 and includes proximal arm segment 56 and distal arm segment 58. Proximal arm segment 56 is generally an elongate tube or bar having a first end portion 60 rotatably coupled to retractor support 46 and a second end portion 62 rotatably coupled to distal segment 58 at elbow 64. End portion 60 of segment 56 permits retractor arm 50 to be rotated relative to post 30 to position a surgical instrument such as distension instrument 34. Segment 56 preferably extends away from and upward from retractor support 46 at an angle of about 45 degrees. As a result, retractor support 46 and adjustment mechanism 48 remain within the easy reach of the physician even when distal segment 58 and distension instrument 34 are elevated to higher heights. As can be appreciated, segment 56 of retractor arm 50 may alternatively extend from retractor support 48 horizontally or at a variety of selected angles.

Distal segment 58 is an elongate tubular member having a first end portion 66, an intermediate portion 68 and a second end portion 70. End portion 66 is rotatably coupled to end portion 62 of segment 56 about elbow 64. Intermediate portion 68 rotates about the axis of segment 58 relative to end portion 66. End portion 70 is pinned to intermediate portion 68 to permit rotational adjustment of end portion 70 relative to portion 68. End portion 70 is configured for being coupled to a surgical instrument such as distension instrument 34. Because end portion 60 of segment 56 is rotatable relative to retractor support 46, because end portion 66 of segment 58 is rotatable relative to end portion 62 of segment 56, and because end portion 70 is rotatable relative to intermediate portion 68 of segment 58, distension instrument 34 may be precisely positioned over surgical table 24 at a plurality of positions. Because intermediate portion 68 of segment 58 is rotatable along an axis of segment 58, the physician may also rotate distension instrument 34 relative to the generally horizontal orientation of segment 58. Thus, the physician may position distension instrument 34 in practically any position and orientation over surgical table 24. Surgical support structure 20 enables a physician to more easily and efficiently distend the abdominal cavity or peritoneum.

According to the method of the present invention, a physician secures a support structure such as surgical instrument support 20 to surgical table 24. The distal end of arm assembly 32 is positioned over a patient on surgical table 24 while post 30 remains stationary. The physician next couples a peritoneal distension instrument extending from arm assembly 32 to a peritoneal structure of the patient. Once the peritoneal instrument is coupled to the peritoneal structure of the patient, the physician raises arm assembly 32 relative to post 30 and surgical table 24 by actuation of adjustment mechanism 48. Actuation of adjustment mechanism 48 by the physician causes retractor support 46 of arm assembly 32 to move upward along post 30 to also raise retractor arm 50 and the distension instrument, thereby distending the peritoneum of the patient. Once arm assembly 32 is raised to a desired height to sufficiently distend the peritoneum, the physician locks arm assembly 32 to post 30 to maintain distension of the peritoneum during surgery.

Figure 2:
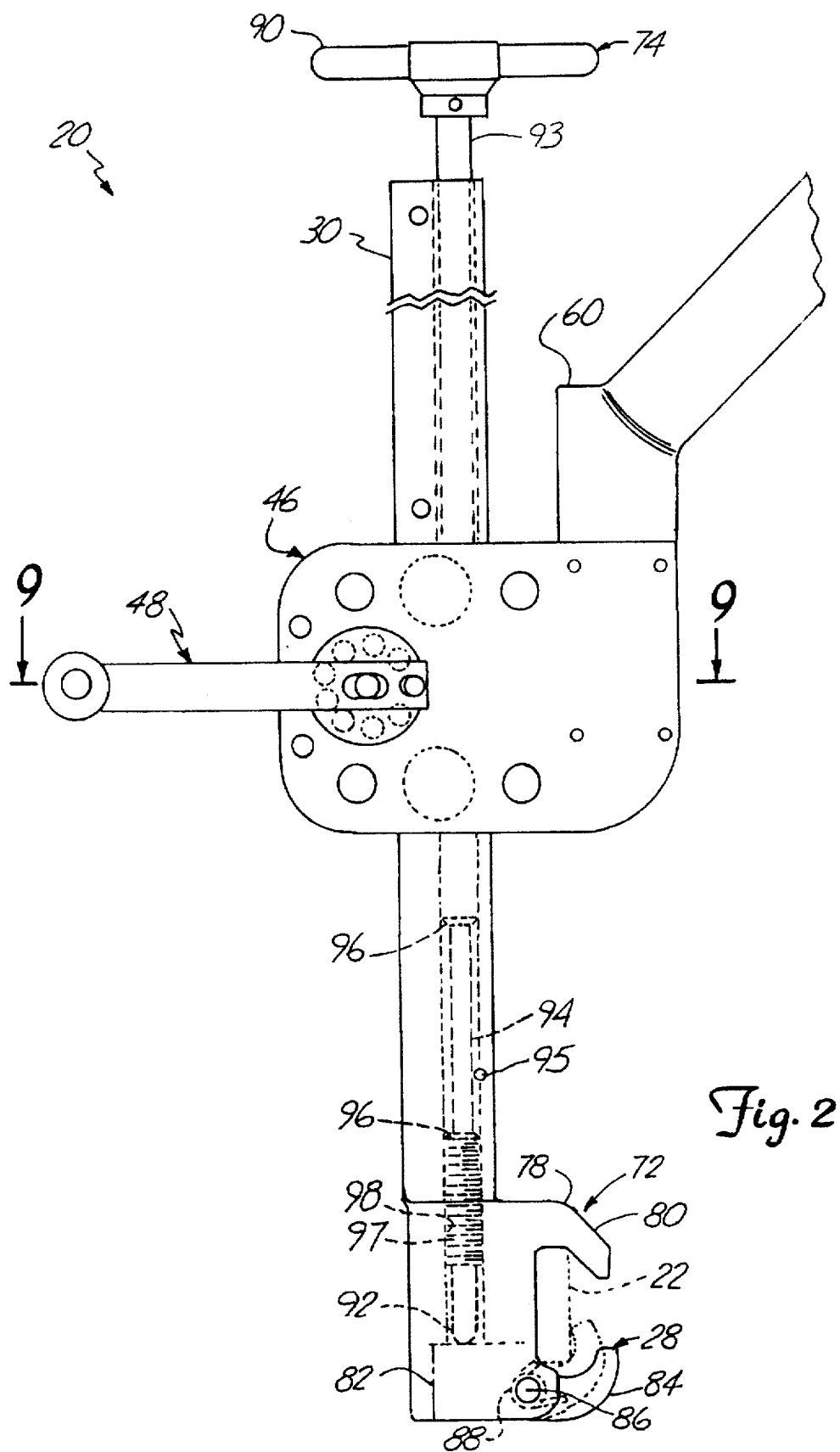
FIG. 2 is a fragmentary side elevational view of the surgical instrument support structure of FIG. 1.

As discussed above, the surgical instrument support structure 20 must be secured to the surgical table by clamping mechanism 28. FIG. 2 is a fragmentary side elevational view of surgical instrument support structure 20 illustrating clamping mechanism 28 in greater detail. Clamping mechanism 28 is substantially similar to the clamping device described in LeVahn et al. U.S. Pat. No. 5,400,772, issued Mar. 28, 1995, assigned to Minnesota Scientific, Inc., St. Paul, Minn., which is hereby incorporated by reference. Clamping mechanism 28 generally includes jaw 72 and tightening mechanism 74. Jaw 72 includes upper member 78 with upper clamping portion 80, lower member 82 with lower clamping portion 84, pivot pin 86 and spring 88. Spring 88 provides a biasing force to upper member 78 and lower member 82 and tends to bias upper and lower clamping portions 80 and 84 away from one another to open jaw 72.

Tightening mechanism 74 pivots lower member 82 about pivot pin 86 so as to clamp side rail 22 between upper and lower members 78 and 82. Tightening mechanism 74 includes shaft 88 and clamping knob or handle 90. Shaft 88 extends through post 30 and has a first end 92, a second end 93 and an intermediate portion 94. End 92 of shaft 88 engages lower member 82 of jaw 72 while end 93 is coupled to handle 90. Intermediate portion 94 extends along a portion of a length of shaft 88 and has an outer diameter narrower than adjacent portions of shaft 88 so as to form upper and lower shoulders 96. During assembly of clamp 28, shaft 88 is inserted through post 30. Pin 95 is pressed into a bore formed through post 30 adjacent to intermediate portion 94. Preferably, pin 95 extends through post 30 close to intermediate portion 94 so as to engage and abut upper and lower shoulders 96 when shaft 88 is vertically moved within post 30. As a result, the smaller diameter of intermediate portion 94 allows shaft 88 to be moved vertically through a range-of-motion constrained by upper and lower shoulders 96. Pin 95 further captivates shaft 88 within post 30 to prevent accidental removal of shaft 88 from post 30.

Shaft 88 preferably includes an exterior threaded portion 97 which threadably engages an interior threaded portion or passage 98 below intermediate portion 94 of post 30. As a result, rotation of handle 90 threads threaded portion 97 of shaft 88 through threaded passage 98 of post 30 to raise and lower end 92 of shaft 88 relative to lower member 82 of jaw 72. Depending upon the direction in which handle 90 is rotated, lower clamping portion 84 of lower member 82 is tightened or untightened about side rail 22. When handle 90 is rotated to force lower end 92 of shaft 88 downward into contact with an upper surface of lower member 82, lower member 82 pivots counter-clockwise about pivot pin 86 to move lower clamping portion 84 towards upper clamping portion 80 and to tighten jaw 72 about side rail 22. Conversely, when handle 90 is rotated so as to raise end 92 of shaft 88 relative to lower member 82, spring 88 causes lower member 82 to pivot clockwise about pivot pin 86 so that lower clamping portion 84 moves away from upper clamping portion 80 to untighten and open jaw 72 about side rail 22.

Because shaft 88 extends upward through post 30 and because handle 90 is located well above side rail 22 and jaw 72, a physician may easily position and clamp surgical instrument support 20 to side rail 22 of surgical table 24 without having to reach below or adjacent to side rail 22 which constitutes an unsterile region. Consequently, clamping mechanism 28 enables the physician to position and adjust support structure 20 without additional sterilization steps or procedures such as regloving. Additional details and advantages of clamping mechanism 28 are further described in LeVahn et al. U.S. Pat. No. 5,400,772.

Figure 3:
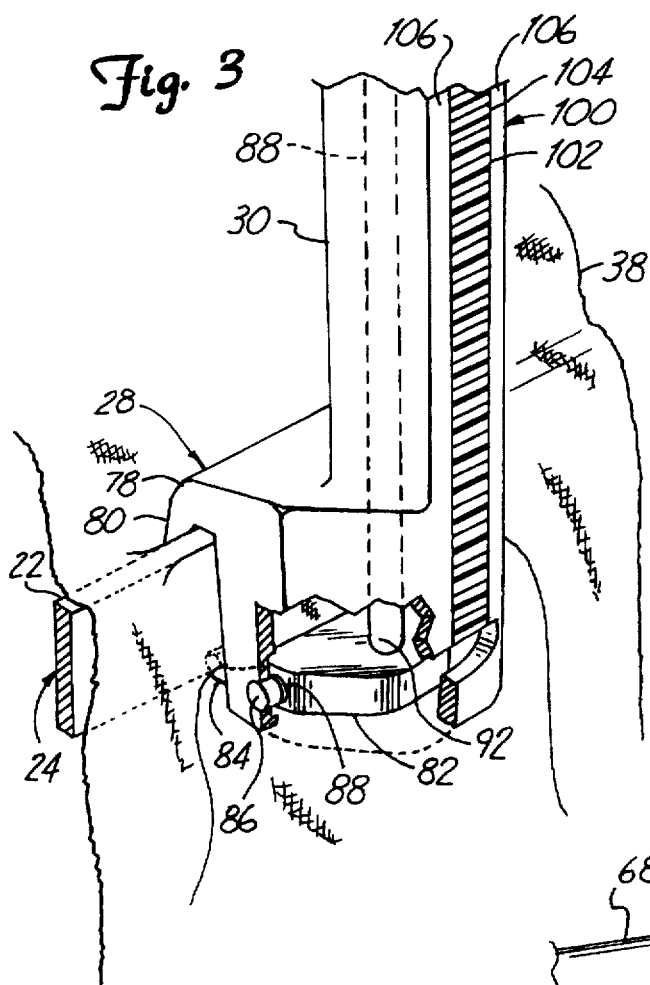
FIG. 3 is an enlarged fragmentary perspective view illustrating the surgical instrument support structure of FIG. 1 clamped to the surgical table.

FIG. 3 is a fragmentary perspective view of post 30 secured over surgical drape 38 to side rail 22 by clamping mechanism 28. Portions of clamping mechanism 28 are removed for illustration purposes. As best shown by FIG. 3, lower end 92 of shaft 88 engages an upper surface of lower member 82 to pivot clamping portion 84 of lower member 82 towards upper clamping portion 80 of upper member 78 about side rail 22.

As further shown by FIG. 3, post 30 includes an elongate track 100 for guiding movement of retractor support 46 (shown in FIG. 2) along post 30. Track 100 preferably extends along a substantial portion of an axial length of post 30 and includes a gear rack 102 formed within an elongate vertical groove 104 defined by shoulder surfaces 106. Preferably, gear rack 102 is an elongate toothed shaft which is secured and inset within a channel of a corresponding elongate receiving shaft having a U-shaped cross-section to form track 100 of post 30. Gear rack 102 enables retractor support 46 to be raised and lowered incrementally along the axis of post 30 by adjustment mechanism 48. Gear rack 102 further enables retractor support 46 to be locked at a selected height along gear rack 102 by adjustment mechanism 48 (shown in FIG. 2).

Shoulder surfaces 106 extend parallel to gear rack 102 on opposite sides of gear rack 102. Shoulder surfaces 106 preferably comprise parallel vertical faces on opposite sides of the channel of the member having a U-shaped cross-section and forming post 30. Shoulder surfaces 106 define groove 104 which maintains a gear member of adjustment mechanism 48 in aligned engagement with gear rack 102. Shoulder surfaces 106 also provide surfaces against which retractor support 46 frictionally engages to impede unintended vertical movement of retractor support 46 relative to post 30 and to lock and secure retractor support 46 at a selected height relative to post 30.

Figure 4:
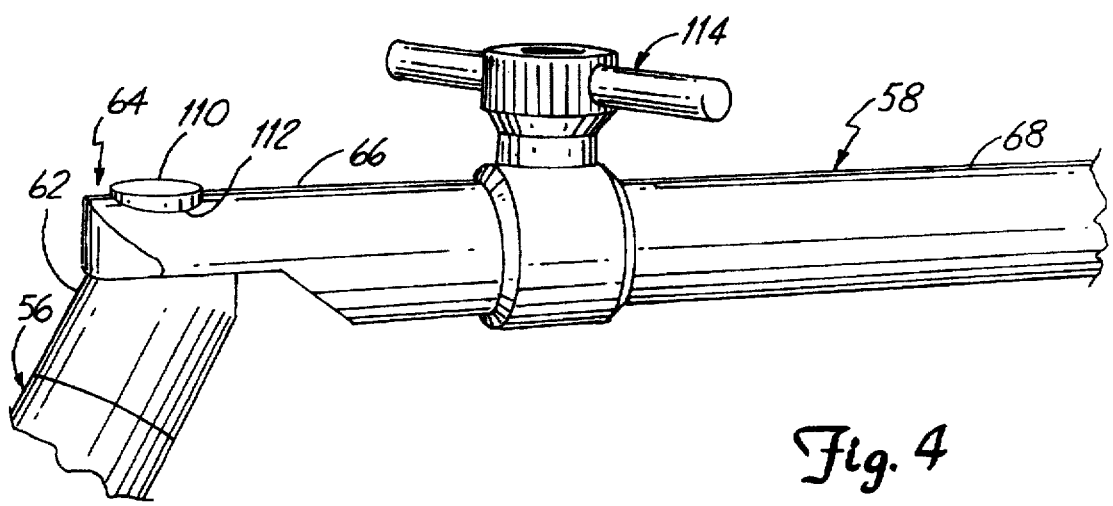
FIG. 4 is an enlarged perspective view of a portion of an arm of the surgical instrument support structure.

Once surgical instrument support 20 is secured to surgical table 24 by clamping mechanism 28, a physician must position the distal end of retractor arm 50 over a patient and couple distension instrument 34 to a peritoneal structure of the patient. As discussed above with respect to FIG. 1, retractor arm 50 includes a plurality of segments which are rotatably coupled to one another to provide precise and accurate positioning of distension instrument 34 over surgical table 24. FIG. 4 is an enlarged perspective view of arm segment 58 interconnected to segment 56 by elbow 64. As best shown by FIG. 4, elbow 64 interconnecting end portions 62 and 66 of arm segments 56 and 58, respectively, comprises a lug or pin 110 extending from end 62 of segment 56 and a bore 112 extending through end portion 66 of segment 58. Pin 110 extends through bore 112 and permits rotation of end portion 66 about pin 110 for positioning arm segment 58.

As further shown by FIG. 4, end portion 66 and intermediate portion 68 of segment 58 are interconnected by rotational coupling mechanism 114. Rotational coupling mechanism 114 permits intermediate portion 68 to rotate relative to end portion 66 out an axis of segment 58. Once intermediate portion 68 is rotated to a desired rotational orientation, mechanism 114 may be tightened to secure intermediate portion 68 in place. As a result, intermediate portion 68 is rotatable relative to segment 56 about elbow 64 and is also rotatable about its own axis to precisely and accurately position a surgical instrument such as distension instrument 34.

FIG. 5 is an exploded perspective view of arm segment 58 illustrating end portion 66, intermediate portion 68 and rotational coupling mechanism 114 in greater detail. End portion 66 is generally an elongate rod having an outer diameter that narrows at one end to form shoulder 16 and lug 118. Lug 118 includes two generally cylindrical bores 120 and 122. Bore 122 preferably has a smaller diameter than bore 120 and is located approximately 90° from bore 120. Bores 120 and 122 of lug 118 receive lugs or pins of rotational coupling mechanism 114.

Intermediate portion 68 is a generally elongate tubular member having an annular wall 124 defining interior 126 and circumferential slot 128. Interior 126 defined by annular wall 124 preferably has an inner diameter sized for receiving lug 118 of end portion 66. Preferably interior 126 is larger than outer diameter of lug 118 so that intermediate portion 68 may rotate about lug 118 when lug 118 is inserted into interior 126 of intermediate portion 68. Circumferential slot 128 is generally C-shaped and extends through a portion of annular wall 124. Slot 128 guides and limits rotation of intermediate portion 68 relative to end portion 66 of segment 58.

Rotational coupling mechanism 114 rotationally joins end portion 66 and intermediate portion 68 and includes collar 130, pin 132, pin 134 and handle 136. Collar 130 is a generally annular shaped member having an outer circumferential surface with a generally flat portion 137 and an inner diameter larger than the outer diameter of intermediate portion 68. Collar 130 further defines bores 138 and 140.

Bore 138 extends through flat portion 137 of collar 130 and is sized for receiving pin 134. Bore 138 preferably has a diameter corresponding to the diameter of bore 120 formed through lug 118. Bore 138 is located so as to align with bore 120 when lug 118 is inserted through collar 130 and into interior 126 of intermediate portion 68.

Bore 140 extends through collar 130 preferably at an angle of about 90° with respect to bore 138. Bore 140 has a diameter sized for receiving pin 132 and is preferably located so as to become aligned with bore 122 formed within lug 118 when lug 118 is inserted through collar 130. Bore 140 provides an insertion opening for inserting pin 132 into lug 118 across pin 134.

Pin 132 is an elongate registered pin having a length less than or equal to a diameter of lug 118 of end portion 66. Pin 132 has a diameter sized for being received through bore 140 of collar 130 and for being located within bore 122 of lug 118 through pin 134 to couple pin 134 to lug 118.

Pin 134 includes bore 142 and threaded portion 144. Bore 142 extends through pin 134 and is sized and located for receiving pin 132. Threaded portion 144 is located towards one end of pin 134 and threadably engages handle 136.

Handle 136 includes a central hub 146 and a pair of arms 148. Hub 146 threadably engages threaded portion 144 of pin 134 and includes a pair of opposite bores 150 which are sized for receiving arms 148.

Upon assembly, lug 118 of end portion 66 extends through collar 130 and fits within interior 126 of end portion 68 so as to align bores 120 and 138 and bores 122 and 140. In addition, bore 120 and bore 138 also align within slot 128 of intermediate portion 68. Collar 130 encircles both lug 118 and intermediate portion 68. Pin 114 extends through bore 138, slot 128 and bore 120. Pin 132 extends completely within bore 122 and within lug 118 through bore 142 of pin 134. Pin 132 joins pin 134 and lug 118 of end portion 66 within interior 126 of intermediate portion 68. As intermediate portion 68 is rotated about lug 118, slot 128 rotates along an about pin 134. Pin 134 engages walls 124 defining slot 128 so as to guide and limit the degree by which intermediate portion 68 may be rotated relative to end portion 66. Pin 134 further engages annular wall 124 to prevent intermediate portion 68 from becoming disconnected from collar 130 and end portion 66.

Once intermediate portion 68 is rotated to a desired rotational orientation relative to end portion 66, the physician may lock end portion 68 in the selected orientation by rotating handle 136. Rotation of handle 136 causes hub 146 to threadably move along threaded portion 144 of pin 134. Continual rotation of handle 136 causes hub 146 to press against flat portion 137 of collar 130 to tighten and clamp collar 130 about intermediate portion 68 and lug 118 to lock intermediate portion 68 in the selected rotational position. Opposite rotation of handle 136 moves hub 146 away from flat surface 137 of collar 130 to unclamp and loosen collar 130 about intermediate portion 68 so that intermediate portion 68 may be rotated for necessary adjustments.

FIG. 5A is an exploded perspective view of arm segment 58a, an alternate embodiment of arm segment 58 illustrated in FIG. 5. Arm segment 58a is similar to arm segment 58 except that arm segment 58a includes rotational coupling mechanism 114a in lieu of rotational coupling mechanism 114 and end portion 66a in lieu of end portion 66. For ease of illustration, those elements of arm segment 58a which are the same as those elements of arm segment 58 are numbered similarly. End portion 66a is similar to end portion 66 except that end portion 66a includes bore 120a and counterbore 151. Bore 120a extends at least partially into lug 118 and is internally threaded for receiving threads of pin 134a. Counterbore 151 extends into lug 118 above bore 120a and is sized for receiving washer 152.

Rotational coupling mechanism 114a rotationally joins end portions 66a and intermediate portion 68 and includes collar 130, washer 152, bolt or pin 134a, washer 153 and handle 136a. Collar 130a is a generally annular shaped member having an outer circumferential surface with a generally flat portion 137a and an inner diameter larger than the outer diameter of intermediate portion 68. Collar 130a defines bore 138a. Bore 138a extends through flat portion 137a of collar 130a and is sized for receiving pin 134a. Bore 138a is located so as to align with bore 120a when lug 118 is inserted through collar 130a into interior 126 of intermediate portion 68.

Pin 134a is an elongated pin having a first end portion 154, a second end portion 155 and an intermediate portion 156. End portion 154 is externally threaded for threadably engaging the interior threads of bore 120a. End portion 155 is located opposite threaded end portion 154 and defines bore 157. Bore 157 extends through end portion 155 and is sized for receiving pin 158 for securing handle 136a to pin 134a. Intermediate portion 156 has a diameter less than the diameter of end portion 154 and end portion 154. Intermediate portion 156 is sized for receiving and capturing washer 152.

Washer 152 is a generally annular shaped ring having an inner diameter larger than the diameter of intermediate portion 158 but smaller than the diameter of end portions 156 and 157 of pin 154. Washer 152 preferably has an outer diameter larger than the diameter of bore 138a extending through collar 130a. Washer 152 is made of a material that is resilient enough to permit positioning of washer 152 past threaded end portion 154. Washer 152 is preferably formed from a flexible material that is strong, lightweight and autoclavable. In the most preferred embodiment, washer 152 is made from Victrex PEEK, a poly(aryletherkeone), a linear aromatic polymer, manufactured by ICI of Great Britain.

Washer 153 is an annular ring having an inner diameter larger than the outer diameter of end portion 157 of pin 154. Washer 153 preferably has an outer diameter larger than the diameter of bore 138. Washer 153 is preferably made from a flexible material that the strong, lightweight and autoclavable. Preferably, washer 153 is made from Victrex PEEK.

Handle 136a includes a central hub 146a, arm 148a and pin 158. Bore 150a extends through hub 146a and is sized for receiving arm 148a. Arm 148a extends through bore 150a so as to provide a pair of opposite arms. Hub 146a further includes bore 159 sized for receiving pin 158.

Upon assembly, washer 152 is placed in counterbore 151. Lug 118 of end portion 66a extends through collar 130a and fits within interior 126 of end portion 68 so as to align bore 120a and bore 138a. Collar 130a encircles both lug 118 and intermediate portion 68. Pin 134a slides freely through bore 138a and is pressed through washer 152 so as to capture washer 152 about intermediate portion 156 between the larger diametered end portions 154 and 155 of pin 134a. Threaded end portion 154 threadably engages interior threads within bore 120a. Washer 153 slides over end portion 155 below bore 157. Pin 158 extends through bore 159 of hub 146a and through bore 156 of pin 134a to couple hub 146a of handle 136a to pin 134a.

As a result, washer 152 is captured between end portions 154 and 155 of pin 134a and prevents pin 134a from being disengaged from collar 130a and from arm segment 58a even when threaded end portion 154 is threadably disengaged from the interior threads of bore 120a. Since the outside diameter of washer 152 is greater than the diameter of bore 138a, washer 152 prevents pin 154 from being pulled back through bore 138a once pin 134a is inserted through bore 138a and through washer 152 into bore 120a. The above described arrangement permanently and rotatably attaches end portion 66a to end portion 68.

As with rotational coupling mechanism 114a, rotational coupling mechanism 114 also permits the physician to lock end portion 68 in a selected orientation relative to end portion 66a by rotating handle 136a. Rotation of handle 136a, causes threaded end portion 155 of pin 134a to threadably move within bore 120a to cause hub 146a to press against washer 153 and collar 130a to tighten and clamp collar 130a about intermediate portion 68 and lug 118 to lock intermediate portion 68 in the selected rotational position. Opposite rotation of handle 136a moves hub 146a away from flat surface 137a of collar 130a to unclamp and loosen collar 130a about intermediate portion 68 so that intermediate portion 68 may be rotated for necessary adjustments.

Figure 6:
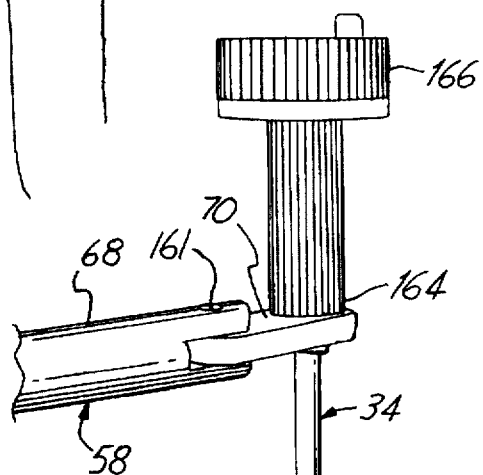
FIG. 6 is an enlarged perspective view of a portion of the arm of the surgical instrument support structure coupled to a distension instrument.

FIG. 6 is an enlarged perspective view of intermediate portion 68 and end portion 70 of segment 58 supporting distension instrument 34. As best shown by FIG. 6, end portion 70 is preferably pinned to intermediate portion 68 by registered pin 161 and is configured for supporting a surgical instrument such as distension instrument 34. As a result, end portion 70 and distension instrument 34 may be rotated relative to intermediate portion 68 for better positioning of distension instrument 34.

Distension instrument 34 is configured for being supported by retractor arm segment 58. Distension instrument 34 generally includes retractor fan 160, shaft 162, mount 164 and actuation knob 166. Retractor fan 160 includes a plurality of retractor blades or plates 170 which overlap one another. As a result, plates 170 may overlap one another so as to have a narrow width to enable retractor fan 160 to be inserted through a single, narrow slit or incision within the abdominal wall. Once inserted, plates 170 are fanned out as shown in FIG. 6 to provide a larger surface area for engaging the abdominal wall during distension of the peritoneum.

As conventionally known, a caming mechanism (not shown) interconnects knob 166 and retractor fan 160 to fan out plates 170 of fan 160. Mount 164 connects distension instrument 34 to end portion 70 of retractor arm segment 58. Shaft 162 is coupled between knob 166 and retractor fan 160. Shaft 162 supports and encloses the caming mechanism and spaces fan 160 from end portion 70 of arm segment 58. Shaft 162 preferably has a length of at least about eight inches. Because shaft 162 has a length of at least about eight inches, retractor fan 160 is sufficiently spaced from retractor arm segment 58 to allow the physician greater accessibility and visibility of the distended peritoneum. In addition, because retractor fan 160 is spaced from retractor arm segment 58 by at least about eight inches, video imaging equipment such as a laparoscope are more easily positioned and inserted by the physician into the peritoneum during surgery.

Figure 7:
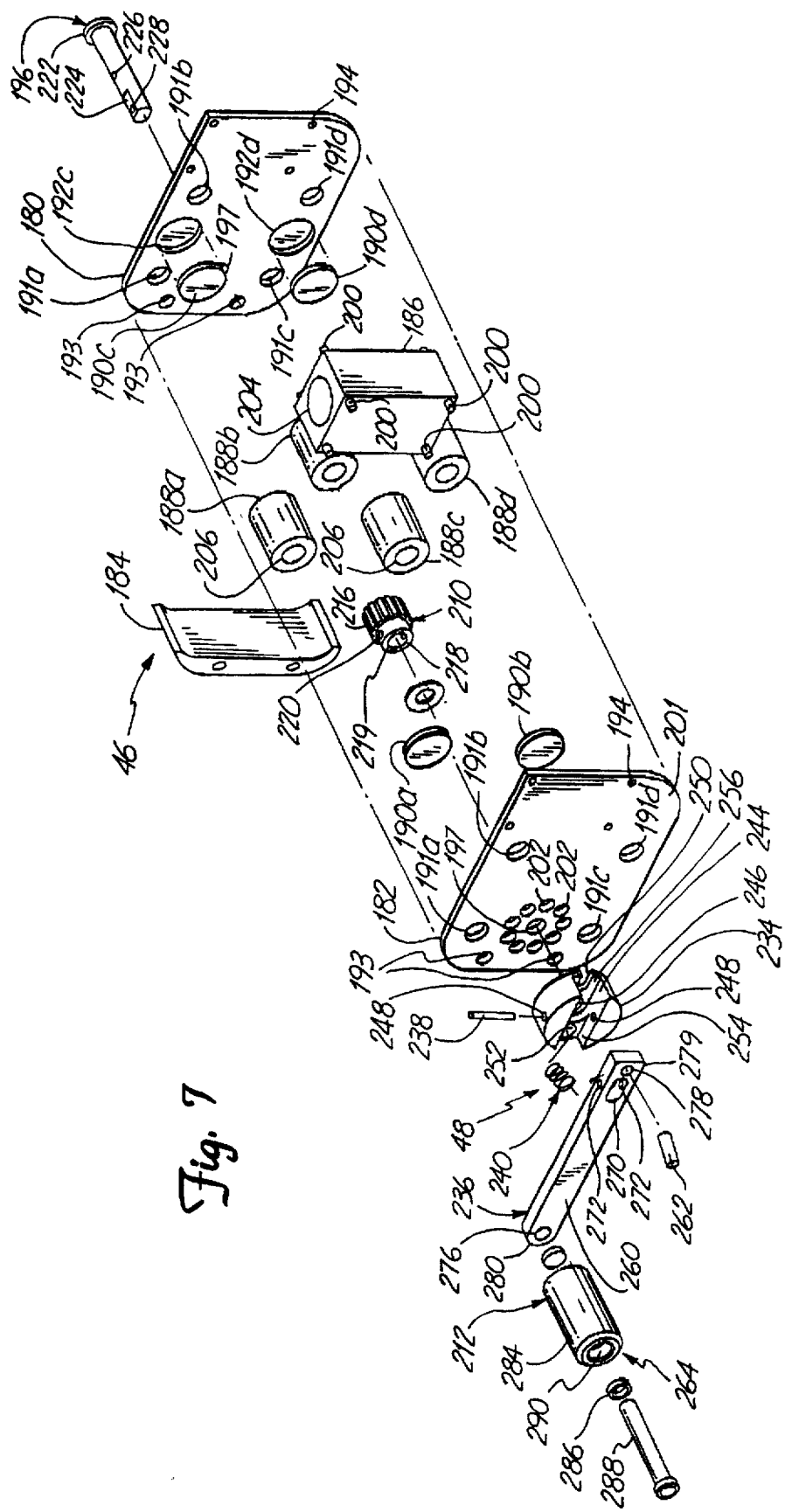
FIG. 7 is an exploded perspective view of a retractor support and an adjustment mechanism of the surgical instrument support structure.

Once retractor arm 50 is precisely and accurately positioned over a patient on surgical table 24 and once distension instrument 34 is coupled to the peritoneal structure of the patient, the physician elevates and distends the peritoneal structure by vertically raising retractor support 46 of arm assembly 32 along post 30 with adjustment mechanism 48. FIG. 7 is an exploded perspective view of retractor support 46 and vertical adjustment mechanism 48. As best shown by FIG. 7, retractor support 46 includes support plates 180, 182, shield 184, support block 186, roller bearings 188a–188d and surface bearings 190a–190d. Plates 180 and 182 are generally flat panels which are assembled opposite one another so as to capture shield 184, block 186, roller bearings 188 and surface bearings 190 therebetween. Plates 180 and 182 include bores 191a–191d, depressions 192a(not shown), 192b(not shown), 192c, 192d, bores 193, bores 194 and axle openings 197. Bores 191a–191d extend through both plates 180 and 182 and are sized for receiving registered pins 195a–195d(shown in FIG. 8), respectively, which support roller bearings 188a–188d, respectively, between plates 180 and 182 in engagement with post 30. Depressions 192a–192d partially extend into plates 180 and 182 from an inner surface of plates 180 and 182. Depressions 192a–192d are sized for partially receiving and capturing surface bearings 190a–190d, respectively. As a result, plates 180 and 182 carry and support surface bearings 190a–190d. Plates 180 and 182 support surface bearings 190a and 190b and surface bearings 190c and 190d, respectively, at a distance apart from one another so that surface bearings 190a, 190b and 190c, 190d engage opposite sides of post 30 when retractor support 46 is movably coupled along post 30 as shown in FIG. 9.

Bores 193 extend through plates 180 and 182 and are aligned with one another for receiving registered pins 199 (shown in FIG. 8) which extend through shield 184 to capture shield 184 between plates 180 and 182 so that shield 184 partially encloses components of adjustment mechanism 48. Bores 194 extend through plates 180 and 182 in alignment with one another and are sized for receiving registered pins 200 which extend from support block 186 so that support block 186 is also captured between plates 180 and 182. Block 186 further defines bore 204 which extends into block 186 and which is sized rotatably receiving end portion 60 of arm segment 56.

Axle openings 197 are in alignment with one another and extend through plates 180 and 182. Axle openings 197 are sized for receiving axle pin 196 so that axle pin 196 is journaled between plates 180 and 182. Axle pin 196 couples adjustment mechanism 48 to retractor support 46.

Plate 182 is similar to plate 180 except that plate 182 further includes a plurality of detents 202 circularly spaced about axle opening 197. Detents 202 at least partially extend into an exterior surface 201 of plate 182. Detents 202 are used for locating and locking retractor support 46 and retractor arm 50 (shown in FIG. 1) at a selected height above surgical table 24. Once assembled, plates 180 and 182, shield 184 and retractor support 186 substantially surround and enclose post 30.

Roller bearings 188a–188d are generally tubular shaped cylinders of a resilient low friction material. Preferably, roller bearings 188a–188d are formed from plastic. In the most preferred embodiment, roller bearings 188a–188d are made from Victrex PEEK, a poly(aryletherketone), a linear aromatic polymer manufactured by ICI of Great Britain. Roller bearings 188a–188d each define a bore 206 which extends through the roller bearing for receiving pin 195 so that roller bearings 188a–188d may be secured between plates 180 and 182. Roller bearings 188a, 188c are spaced from roller bearings 188b, 188d, respectively, so that roller bearings 188a, 188c and roller bearings 188b, 188d engage opposite sides of post 30 when retractor support 46 is movably coupled to post 30. Roller bearings 188a–188d impede lateral or sideways movement of support 46 and arm 50 about post 30 to stabilize support 46 and arm 50. Roller bearings 188a, 188d are preferably vertically spaced apart to reduce unintended rotation of support 46 and arm 50 about post 30 for increased stabilization of support 46 and arm 50. At the same time, bearings 188a and 188d are spaced close enough together so as to cause post 30 to bind between bearings 188a, 188d when sufficient torque is placed upon retractor support 46 by force applied to retractor arm 50. Preferably, roller bearings 188a and 188d have a vertical spacing to a horizontal spacing ratio (aspect ratio) of less than or equal to about two to one. The aspect ratio combined with the level of friction between bearings 188a, 188d, and post 30 cause retractor support 46 to bind with post 30 when retractor support 46 experiences torque from forces applied to retractor arm 50. Roller bearings 188b and 188c are similarly spaced from one another. As can be appreciated, the aspect ratio may be increased or decreased with corresponding decreases or increases in friction between bearings 188a, 188d, and post 30, respectively. As can further be appreciated, bearings 188a and 188d or bearings 188b and 188c may be omitted in favor of a single pair of diagonally spaced roller bearings.

Surface bearings 190a–190d are preferably flat circular surfaces of resilient low friction material such as plastic. Surface bearings 190a–190d are preferably made from Victrex PEEK, a poly(aryletherketone), a linear aromatic polymer, manufactured by ICI of Great Britain. Surface bearings 190a and 190b are captured and supported by depressions 192a and 192b, respectively (not shown), of plate 182 while surface bearings 190c and 190d are captured and supported by depressions 192c and 192d, respectively, of plate 180. Once retractor support 46 is coupled to post 30, surface bearings 190a, 190b and surface bearings 190c, 190d engage opposite surfaces of post 30 to impede vertical movement of retractor support 46 and retractor arm 50 relative to post 30. Surface bearings 190a–190d also impede lateral movement to stabilize retractor support 46 and retractor arm 50 about post 30.

As best shown by FIG. 7, adjustment mechanism 48 includes circular gear 210, axle pin 196 and crank 212. Circular gear 210 is a generally cylindrical pinion member having teeth 216, end portion 218 and bore 219. End portion 218 defines pin hole 220. Pin hole 220 through end portion 218 and is sized for receiving a registered pin 221 (shown in FIG. 9) which also extends through bore 226 of axle pin 196 to couple circular gear 210 to axle pin 196 when axle pin 196 is inserted through bore 219. Bore 219 concentrically extends through circular gear 210 and has an inner diameter sized for receiving axle pin 196. Circular gear 210 is rotatably supported between plates 180 and 182 by axle pin 196.

Axle pin 196 rotatably supports circular gear 210 between plates 180 and 182. Axle pin 196 is an elongate bolt which includes head 222, flat end 224 and bores 226, 228. Pin 196 extends through apertures 197 of plates 180 and 182. Head 222 abuts plate 180 while flat end 224 projects from plate 182 for coupling with crank 212. Bore 226 extends through pin 196 and has an inner diameter sized for receiving pin 221 (shown in FIG. 9). Bore 228 extends through flat end 224 and is sized for receiving registered pin 238 (shown in FIG. 9) to pin crank 212 to flat end 224 of pin 196. Rotation of crank 212 rotates axle pin 196 and circular gear 210.

Crank 212 is coupled to axle pin 196 for rotating axle pin 196 and circular gear 210. In addition to rotating circular gear 210, crank 212 also engages plate 182 of retractor support 46 to prevent rotation of circular gear 210 and to lock circular gear 210 relative to gear rack 102 (shown in FIG. 3). Crank 212 generally includes crank mount 234, crank arm assembly 236, pin 238 and biasing means 240. Crank mount 234 is a generally circular, surface shaped member defining channel 244, aperture 246, bores 248, notch 250 and capture 252. Channel 244 extends partially into and across a front face of crank mount 234 to form inner side walls 254 and floor 256. Slot 244 has a depth and a width sufficient for receiving crank arm assembly 236. Aperture 246 concentrically extends through crank mount 234 within slot 244. Aperture 246 is sized for receiving axle pin 196 so that axle pin 196 may be inserted through aperture 246 and coupled to crank arm assembly 236. Bores 248 extend through crank mount 234 in a direction generally perpendicular to direction of slot 244 above floor 256. Bores 248 are in alignment with one another and are sized for receiving pin 238. Capture 252 partially extends into floor 256 within channel 244 of crank mount 234. Capture 252 is located on an opposite end of channel 244 relative to notch 250. Capture 252 supports and receives biasing means 240. Notch 250 extends through floor 256 of crank mount 234 opposite capture 252. Notch 250 is sized for permitting a portion of crank arm assembly 236 to extend through crank mount 234 into engagement with detents 202 in plate 182.

Crank arm assembly 236 includes crank arm 260, pin 262 and handle 264. Crank arm 260 is a generally elongate, flat member having a width sized for being receiving within channel 244 and defining slot 270, bores 272, bore 276 and bore 278. Slot 270, bores 272 and bore 276 are each defined in a first end 279 which is positioned within channel 244 of crank mount 234. Slot 270 is a generally elongate, oval-shaped opening which extends through arm 260 and is sized for receiving flat end 224 of axle pin 196. Slot 270 has a length longer than flat end 224 of axle pin 196 so that arm 260 may pivot around flat end 224. Bores 272 are in alignment with one another and extend through arm 260 across slot 270 in a direction generally perpendicular to an axis of slot 270. Bores 272 are sized for receiving pin 238. Bore 276 extends through a second end 280 of arm 260 and is sized for receiving bolt 288 of handle 264. Bore 278 extends through first end 279 of arm 260 on a side of slot 270 opposite bore 276. Bore 278 is sized for receiving pin 262.

Pin 262 is an elongate member which extends through bore 278 and projects from bore 278 for engaging detents 202 within plate 182. As can be appreciated, pin 262 may be fixedly coupled to first end 278 by any of a variety of coupling mechanisms. In addition, pin 262 may alternatively be integrally formed as part of arm 260.

Handle 264 is coupled to end 280 of arm 260 and generally includes cylinder 284, washer 286 and bolt 288. Cylinder 284 includes a hollow, concentric bore 290 which has an inner diameter sized for receiving bolt 288. Bolt 288 extends through washer 286 and through bore 290 and is press fit within bore 276 of arm 260 to rotatably couple cylinder 284 to arm 260.

Upon assembly of adjustment mechanism 48, end 279 of crank arm 260 is located within channel 244 so as to align slot 270 and aperture 246 and to align bores 248 and bores 272. Axle pin 196 extends through plates 180 and 182 and is coupled to circular gear 210 by registered pin 221 (shown in FIG. 9) which extends through bores 220 and 226. Axle pin 196 is journaled relative to plates 180 and 182 so that rotation of axle pin 196 causes rotation of circular gear 210. Flat end 224 of axle pin 196 extends through crank mount 234 and through aperture 246 of slot 270 within arm 260 so as to align bore 228 with bores 248 and 272. Pin 238 extends through bores 248, through bores 272 and through bore 228 of axle pin 196 to secure flat end 224 of axle pin 196 to crank mount 234 and arm 260 and to pivotally support arm 260 about pin 238 within channel 244 of crank mount 234. As a result, crank arm 260 pivots about pin 238 to pivot pin 262 between a first position in which pin 262 engages one of detents 202 to prevent rotation of arm 260 and a second position in which pin 262 is retracted and withdrawn from detents 202 to permit rotation of arm 260 by handle 264.

Biasing means 240 preferably comprises a spring. As can be appreciated, a variety of biasing mechanisms may be alternatively used. Bias means 240 is located within capture 252 between floor 244 of crank mount 234 and a corresponding capture 293 (shown in FIG. 9) formed within arm 260. Biasing means 240 biases first end 279 and pin 262 towards the first position in which pin 262 is engagement with one of detents 202. Compression of biasing means 240 by actuation of arm 260 pivots pin 262 out of engagement with detents 202 to permit arm 260 to be rotated by handle 264.

Rotation of arm 260 by handle 264 causes rotation of crank mount 234 and rotation of circular gear 210. Rotation of crank mount 234 rotates notch 250 about an axis of axle pin 196 so as to bring notch 250 and pin 262 into alignment with a next succeeding detent 202.

Figure 8:
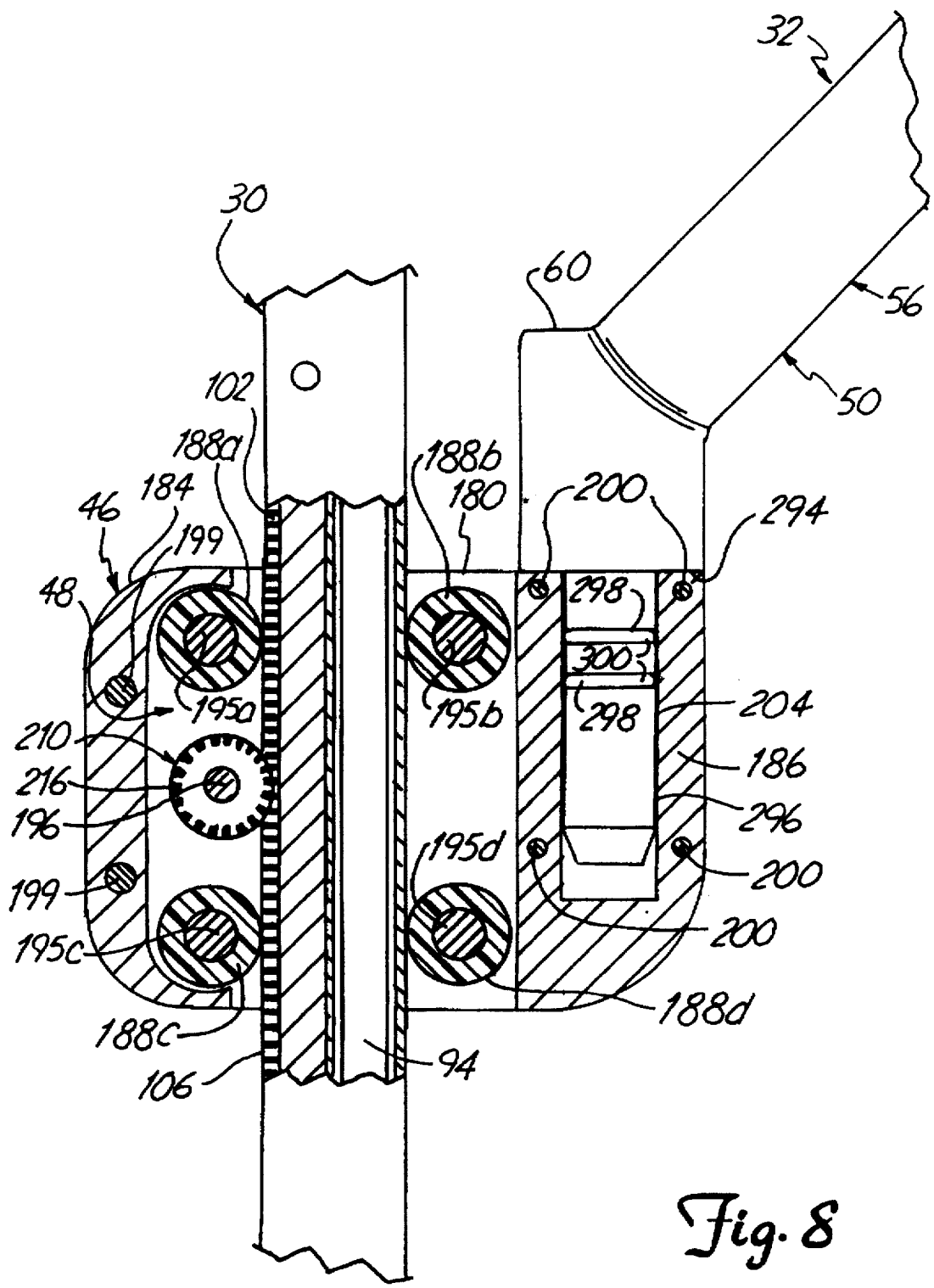
FIG. 8 is a cross-sectional view of the retractor support coupled to a post and a portion of the arm of the surgical instrument support structure.
Figure 9:
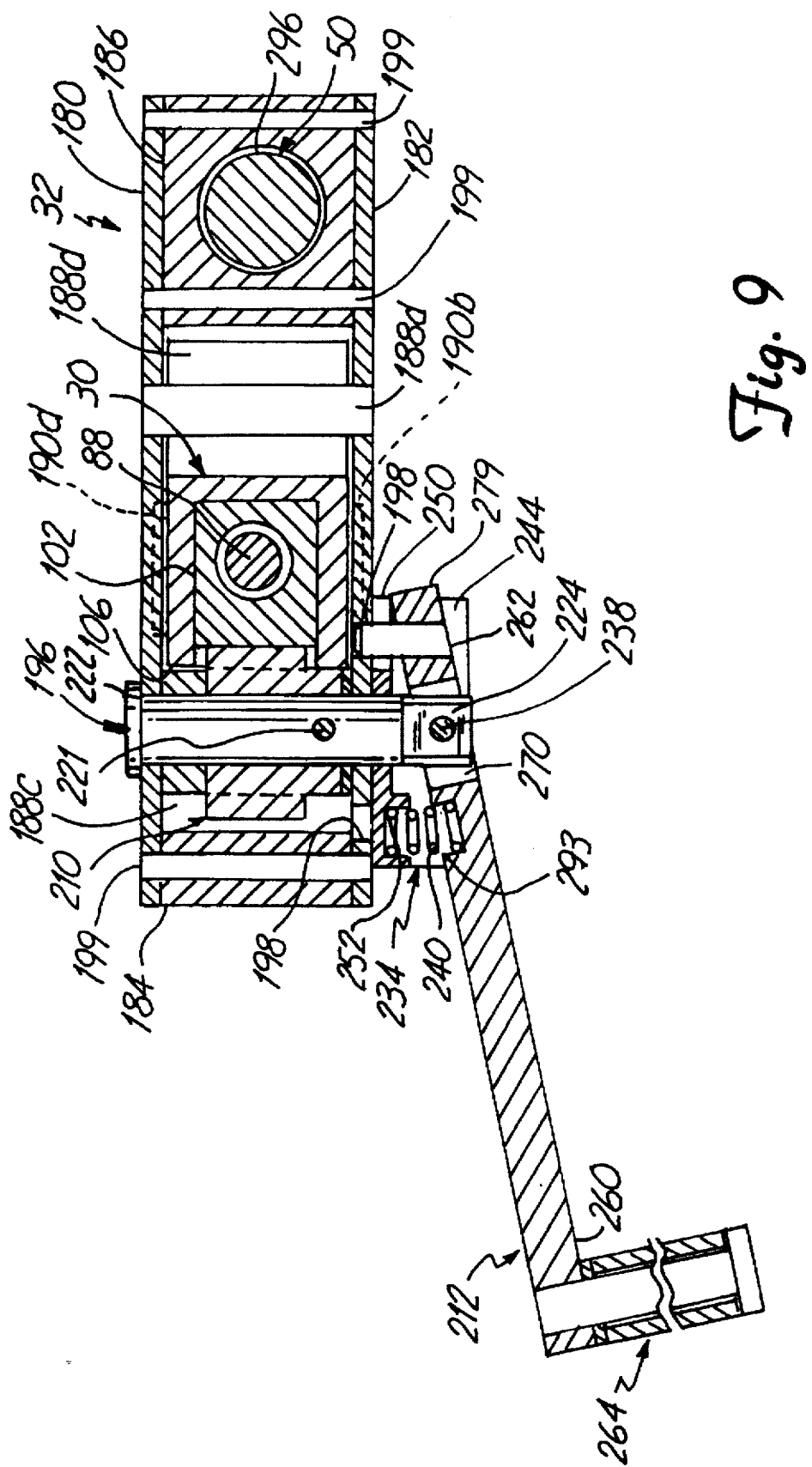
FIG. 9 is a cross-sectional view of the surgical instrument support structure taken along line 9—9 of FIG. 2.

FIG. 8 is a fragmentary cross-sectional view of post 30 and arm assembly 32 illustrating retractor arm 50 coupled to retractor support 46 and further illustrating retractor support 46 movably coupled along post 30. As best shown by FIG. 8, end portion 60 of arm segment 50 has an outer diameter which narrows to form shoulder 294 and lug 296. Lug 296 projects from end portion 60 and has an outer diameter sized for fitting within bore 204 of support block 186 of retractor support 46. Lug 296 fits within bore 204 and shoulder 294 rests upon support block 186 to permit rotation of arm assembly 50 about the axis of lug 296 within bore 204. In the preferred embodiment illustrated, lug 296 additionally includes a pair of circumferential grooves 298 located towards end portion 60. Grooves 298 receive 0-rings 300. 0-rings 300 encircle lug 296 and engage interior surfaces of bore 204 to maintain lug 286 within bore 204 and to prevent withdrawal of lug 296 from bore 204 of retractor support 46.

As further illustrated by FIG. 8, retractor support 46 frictionally engages post 30 while circular gear 210 of adjustment mechanism 48 engages gear rack 102 of post 30 to provide smooth, controlled, incremental, vertical adjustment of retractor support 46 and retractor arm 50 along post 30. Roller bearings 188a and 188c engage shoulders 106 adjacent gear rack 102 while roller bearings 188b and 188d engage a surface opposite shoulders 106. Because roller bearings 188a and 188d are diagonally spaced from one another with an aspect ratio not greater than two to one, downward force applied to retractor arm 50 and support block 186 of retractor support 46 applies a resulting clockwise torque against post 30. Because of the friction between bearings 188a, 188d and post and because the aspect ratio is not greater than about two to one, the torque tends to bind retractor support 46 to post 30 to lock retractor support 46 and retractor arm 50 in position. Consequently, roller bearings 188a and 188d, as well as roller bearings 188b and 188c, impede unintended vertical movement of retractor arm 50, once a vertical height of retractor arm 50 is set. Roller bearings 188a-188d also stabilize retractor support 46 about post 30.

Circular gear 210 is journaled between plates 180 and 182 (shown in FIG. 7) by axle pin 196 to allow circular gear 210 to rotate while in engagement with gear rack 102 and retractor support 46. Because retractor support 46 is coupled to gear 210, rotation of circular gear 210 raises and lowers retractor support 46 and retractor arm 50 along gear rack 102 of post 30 to distend the peritoneum or to adjust the height of distension instrument 34 (shown in FIG. 1).

FIG. 9 is a cross-sectional view of surgical instrument support structure 20 taken along lines 9—9 of FIG. 2. FIG. 9 illustrates assembled retractor support 46 and adjustment mechanism 48 in greater detail. As best shown by FIG. 9, axle pin 196 is rotatably journaled to plates 180 and 182 and is fixedly coupled to circular gear 210 by registered pin 238. Axle pin 196 rotatably supports circular gear 210 in engagement with gear rack 102. As a result, rotation of circular gear 210 by crank 212 raises and lowers retractor support 46 and retractor arm 50 of arm assembly 32 vertically along post 30.

Crank 212 is coupled to axle pin 196 by registered pin 238 which pins or joins both crank mount 234 and arm 260 to axle pin 196. As a result, rotation of crank 212 rotates axle pin 196 and circular gear 210 along gear rack 102 to vertically adjust the height of retractor support 46 of arm assembly 32.

As also shown by FIG. 9, crank arm 260 of crank 212 pivotally supports registered pin 262 about pin 238 within channel 244 of crank mount 234. Crank arm 260 may be pivoted about registered pin 238 to pivot pin 262 into one of detents 202 within plate 182 to prevent rotation of crank 212, axle pin 196 and circular gear 210. By preventing rotation of crank 212 and circular gear 210, pin 262 releasably locks retractor support 46 of arm assembly 32 at a selected height relative to post 30. Conversely, crank arm 260 may be pivoted to pivot pin 262 out of engagement with detents 202 to allow crank 212 and circular gear 210 to be rotated to vertically adjust the height of retractor support 46 relative to post 30. Biasing means 240 is captured between capture 252 and capture 293 and biases pin 262 towards plate 182 so that upon circular alignment of pin 262 and one of detents 202, pin 262 is forced into an aligned detent 202. As a result, even if pin 262 becomes accidentally dislodged from a selected detent 202, biasing means 240 biases pin 262 into the next succeeding detent 202 to limit accidental, vertical movement of arm assembly 32.

Because crank 212 rotates circular gear 210 and also pivots pin 262 into engagement with one of detents 202, crank 212 allows a physician to vertically adjust the height of arm assembly 32 and further permits the physician to lock arm assembly 32 at a desired height relative to post 30 by simply grasping and moving a single component such as crank 212. As a result, vertical adjustment of arm assembly 32 relative to post 30 does not tie up the physician's hands and is simple, quick and efficient. Moreover, because crank 212 of adjustment mechanism 48 remains well above side rail 22 of surgical table 24 (shown in FIG. 1), adjustment of arm assembly 32 and distension instrument 34 does not require a physician to reach below his or her waist or side rail 22, thereby eliminating additional sterilization procedures otherwise required.

In conclusion, the surgical instrument support structure of the present invention enables a physician to more easily and efficiently extend a peritoneum of a patient for surgery. Clamping mechanism 28 enables the physician to easily clamp the surgical instrument support structure to a surgical table and over the surgical drape without reaching or bending below waist level or surface of the table. Once the instrument support structure is secured to the surgical table, retractor arm 50 of the present invention permits the physician to accurately locate a distension instrument relative to the patient. In particular, arm segment 56 rotates about retractor support 46, arm segment 58 rotates about elbow 64 and end portion 70 of arm segment 58 rotates about end 154. In addition, intermediate portion 68 and end portion 70 of arm segment 58 rotate about an axis of arm segment 58 relative to end portion 66 to allow the physician to further adjust distension instrument 34. Because distension instrument 34 has a shaft having a length of at least about eight inches, retractor fan 160 is sufficiently spaced from retractor arm 50 to allow the physician greater visibility and accessibility to the peritoneum during surgery.

After distension instrument 34 has been coupled to a peritoneum structure of the patient, the surgical instrument support structure of the present invention enables the physician to easily and accurately raise or lower distension instrument 34 to distend the peritoneum. Because arm assembly 32 moves vertically relative to post 30 above table 24, adjustment of arm assembly 32 does not require the physician to bend over or reach below his or her waist or the side rail of the surgical table which is generally viewed as being unsterile. Because retractor support 46 carries retractor arm 50 and includes bearings which frictionally engage opposite surfaces of post 30 at all times, retractor support 46 and retractor arm 50 are securely and stably coupled to post 30 free from vibration and unintended movement.

In addition, the surgical instrument support structure allows the physician to easily and securely lock retractor support 46 and retractor arm 50 in place at a desired height above the surgical table. Because the roller bearings have an aspect ratio of less than or equal to about two to one, the roller bearings tend to bind arm assembly 32 to post 30 at a selected height. Adjustment mechanism 48 of surgical instrument support structure 20 enables the physician to vertically adjust the height of arm assembly 32 relative to post 30 and to lock arm assembly 32 to post 30 at a preselected height by simply grasping and moving handle 264 to rotate circular gear 210 and raise arm assembly 32 relative to post 30 and to lock circular gear 210 in place. Because biasing means 240 biases pin 262 into engagement with one of the detents 202, even if pin 262 becomes accidentally dislodged from a selected detent 202, biasing means 240 biases pin 262 into the next succeeding detent to limit accidental vertical movement of arm assembly 32. Furthermore, because adjustment mechanism 48 includes a plurality of detents which are in circular alignment with the pin, arm assembly 32 may be incrementally adjusted and locked at a multitude of vertical heights relative to table 24 to provide the physician with increased flexibility in the degree at which the peritoneum is distended. Consequently, adjustment mechanism 48 allows the physician to accurately, precisely and incrementally raise and lower arm assembly 32 relative to post 30 as desired.

For purposes of illustration, the present invention has been depicted in FIGS. 1–9 for use with an improved multi-segmented retractor arm and an improved distension instrument. However, as can be appreciated, the present invention may also be used in conjunction with a variety of differently configured vertical posts and arm assemblies. Moreover, the present invention may be alternately configured to support any of a variety of distension instruments as well as other surgical instruments.

Although the present invention has been described with reference to preferred embodiments, workers skilled in the art will recognize that changes may be made in form and detail without departing from the spirit and scope of the invention.

What is claimed is:

1. A method for peritoneal distension comprising the steps of:

providing a support structure on a surgical table, the support structure including a substantially vertical post and an arm assembly;

positioning a distal end of the arm assembly over a patient on the surgical table while the vertical post remains stationary;

coupling a peritoneal distension instrument extending from the arm assembly to a peritoneal structure of the patient;

vertically raising the arm assembly while the post remains stationary relative to the surgical table, thereby distending the peritoneum of the patient; and locking the arm assembly to the vertical post at a preselected height.

2. The method of claim 1 wherein locking the arm assembly to the vertical post includes:

placing a load on the distal end of the arm assembly to frictionally bind the arm assembly to the vertical post at a selected height.

3. The method of claim 1 wherein the vertical post includes a gear rack along its axis, wherein the arm assembly includes a gear member movably coupled to the arm assembly and engaging the gear rack and wherein the step of locking the arm assembly to the vertical post includes:

locating a pin coupled to the gear member within a detent defined by the arm assembly to prevent movement of the gear member and to lock the arm assembly to the vertical post at a selected height.

4. The method of claim 1 wherein the vertical post includes a gear rack and wherein the arm assembly includes a circular gear member movably coupled to the arm assembly and engaging the gear rack, wherein the step of vertically raising the arm assembly includes:

moving the circular gear member, whereby movement of the gear member raises the arm assembly relative to the gear rack.

5. The method of claim 1 further including the step of:

rotating a distal portion of the arm assembly about an axis of the distal portion to relocate the distal portion relative to the peritoneum of the patient.

6. A method for peritoneal distension comprising the steps of:

providing a support structure on a surgical table, the support structure including a substantially vertical post and an arm assembly wherein the arm assembly includes a circular gear member movably coupled to the arm assembly and engaging the gear rack;

positioning a distal end of the arm assembly over a patient on the surgical table while the vertical post remains stationary;

coupling a peritoneal distension instrument extending from the arm assembly to a peritoneal structure of the patient; and vertically raising the arm assembly while the post remains stationary relative to the surgical table by moving the circular gear member, whereby movement of the gear member raises the arm assembly relative to the gear rack, thereby distending the peritoneum of the patient.

7. The method of claim 6 further including the step of:

locking the arm assembly to the vertical post at a preselected height.

8. The method of claim 7 wherein locking the arm assembly to the vertical post includes:

placing a load on the distal end of the arm assembly to frictionally bind the arm assembly to the vertical post at a selected height.

9. The method of claim 7 wherein the vertical post includes a gear rack along its axis, wherein the arm assembly includes a gear member movably coupled to the arm assembly and engaging the gear rack and wherein the step of locking the arm assembly to the vertical post includes:

locating a pin coupled to the gear member within a detent defined by the arm assembly to prevent movement of the gear member and to lock the arm assembly to the vertical post at a selected height.

10. The method of claim 6 further including the step of:

rotating a distal portion of the arm assembly about an axis of the distal portion to relocate the distal portion relative to the peritoneum of the patient.

* * * * *

UNITED STATES PATENT AND TRADEMARK OFFICE
CERTIFICATE OF CORRECTION

PATENT NO. : 5,704,900
DATED : JANUARY 6, 1998
INVENTOR(S) : WALTER J. DOBROVOLNY, STEVEN M. LEVAHN

It is certified that error appears in the above-identified patent and that said Letters Patent is hereby corrected as shown below:

Col. 11, line 42, after "Pin hole 220", insert --extends--

Signed and Sealed this

Twenty-seventh Day of October, 1998

Attest:

BRUCE LEHMAN

Attesting Officer   Commissioner of Patents and Trademarks